US011014086B2

(12) United States Patent
Bhatt et al.

(10) Patent No.: US 11,014,086 B2
(45) Date of Patent: May 25, 2021

(54) SENSOR ARRANGEMENT FOR ANALYZING SUBSTANCES IN A MATERIAL AND METHOD FOR OPERATING SUCH A SENSOR ARRANGEMENT

(71) Applicant: Technische Universität München, Munich (DE)

(72) Inventors: Vijay Deep Bhatt, Munich (DE); Saumya Joshi, Munich (DE); Paolo Lugli, Hallbergmoos (DE)

(73) Assignee: Technische Uniersität München, Munich (DE)

( * ) Notice: Subject to any disclaimer, the term of this patent is extended or adjusted under 35 U.S.C. 154(b) by 147 days.

(21) Appl. No.: 16/051,160

(22) Filed: Jul. 31, 2018

(65) Prior Publication Data

US 2019/0030531 A1 Jan. 31, 2019

(30) Foreign Application Priority Data

Jul. 31, 2017 (DE) .......................... 102017213158.6

(51) Int. Cl.
*G01N 27/00* (2006.01)
*B01L 3/00* (2006.01)
*G01N 33/487* (2006.01)
*G01N 27/02* (2006.01)
*G01N 15/12* (2006.01)
(Continued)

(52) U.S. Cl.
CPC ... *B01L 3/502715* (2013.01); *B01L 3/502792* (2013.01); *B03C 5/026* (2013.01); *G01N 15/1227* (2013.01); *G01N 27/00* (2013.01); *G01N 27/02* (2013.01); *G01N 33/48721* (2013.01); *G01N 33/48735* (2013.01); *B01L 2300/0645* (2013.01); *B01L 2300/0663* (2013.01); *B01L 2400/0415* (2013.01); *B01L 2400/0427* (2013.01); *C12Q 1/6869* (2013.01); *C12Q 2523/303* (2013.01);
(Continued)

(58) Field of Classification Search
CPC .. G01N 27/00; G01N 33/48721; G01N 27/02; G01N 15/1227; C12Q 1/6869; C12Q 2565/607; C12Q 2523/303; C12Q 2563/116
USPC .......................................... 324/61, 65, 71.1
See application file for complete search history.

(56) References Cited

U.S. PATENT DOCUMENTS 6,437,551 B1 8/2002 Krulevitch et al.
2004/0189311 A1 9/2004 Glezer et al.
(Continued)

FOREIGN PATENT DOCUMENTS

DE 10 2015 219 023 B3 2/2017

*Primary Examiner* — Raul J Rios Russo
(74) *Attorney, Agent, or Firm* — Dascenzo Gates Intellectual Porperty Law, P.C.

(57) ABSTRACT

The present disclosure relates to a sensor arrangement (1) for analyzing substances in a material, comprising a substrate (2), a first reception area (5) for receiving a first material, an electronic component sensor (3), a test area (4) that is in contact with the electronic component sensor (3), and a control device (10). The first reception area (5) and the test area (4) are arranged on the substrate (2). The control device (10) is configured for controlling the first reception area (5) and/or the test area (4) to move a portion of the first material from the first reception area (5) into the test area (4). Further, the present disclosure relates to a method for operating such a sensor arrangement (1).

12 Claims, 7 Drawing Sheets

(51) Int. Cl.
  *B03C 5/02*     (2006.01)
  *C12Q 1/6869*   (2018.01)
  *G01N 15/10*    (2006.01)

(52) U.S. Cl.
  CPC .. *C12Q 2563/116* (2013.01); *C12Q 2565/607* (2013.01); *G01N 15/1031* (2013.01)

(56)         References Cited

U.S. PATENT DOCUMENTS

| | | |
|---|---|---|
| 2011/0100820 A1 | 5/2011  | Bachmann et al. |
| 2012/0091003 A1 | 4/2012  | Chuang et al. |
| 2012/0190040 A1 | 7/2012  | Telebpour et al. |
| 2012/0235080 A1 | 9/2012  | Hong et al. |
| 2012/0244572 A1 | 9/2012  | Greenbaum et al. |
| 2012/0325665 A1 | 12/2012 | Chiou et al. |
| 2013/0030510 A1 | 1/2013  | Han et al. |
| 2013/0114120 A1 | 5/2013  | Jung et al. |
| 2013/0126358 A1 | 5/2013  | Lee et al. |
| 2013/0260447 A1 | 10/2013 | Link |
| 2014/0057283 A1 | 2/2014  | Wang et al. |
| 2014/0278136 A1 | 9/2014  | Shamsheyeva et al. |
| 2014/0305799 A1 | 10/2014 | Link et al. |
| 2014/0363823 A1 | 12/2014 | Goldberg et al. |
| 2015/0008123 A1 | 1/2015  | Cheng et al. |
| 2015/0107998 A1 | 4/2015  | Fobel et al. |
| 2015/0174577 A1 | 6/2015  | Srinivasan et al. |
| 2017/0097331 A1 | 4/2017  | Lugli et al. |
| 2017/0102370 A1* | 4/2017 | Alber ............... G01N 21/78 |
| 2017/0325737 A1* | 11/2017 | Olguin Alvarez ............... A61B 5/14517 |
| 2017/0350851 A1* | 12/2017 | Sauerbrey ......... G01N 33/49 |
| 2018/0003614 A1* | 1/2018 | Sait M. A. ......... G01N 15/0266 |
| 2018/0021777 A1* | 1/2018 | Giri .................. G01N 15/0266 422/73 |
| 2019/0187148 A1* | 6/2019 | Lo .................... G01N 27/414 |
| 2020/0070112 A1* | 3/2020 | Darmstaedter ... B01F 15/00214 |
| 2020/0172849 A1* | 6/2020 | Takemura ............. C12M 1/00 |

\* cited by examiner

SENSOR ARRANGEMENT FOR ANALYZING SUBSTANCES IN A MATERIAL AND METHOD FOR OPERATING SUCH A SENSOR ARRANGEMENT

RELATED APPLICATION

The present application claims priority under 35 U.S.C. § 119 to similarly entitled German Patent Application No. 102017213158.6, which was filed on Jul. 31, 2017 and the complete disclosure of which is hereby incorporated by reference.

FIELD OF THE DISCLOSURE

The present disclosure is directed generally to sensor arrangements for analyzing substances in a material, and more particularly to sensor arrangements and methods for analyzing biological substances in a material.

BACKGROUND OF THE DISCLOSURE

Known from the state of the art are electrical methods for examining fluidic microsystems. Thus, what is for example known from DE 10 2015 219 023 B3 is an impedance method. Challenges with known sensor arrangements and methods include the time and materials needed to accurately calibrate the sensors. This may be particularly challenging when the sensors are configured to analyze biological substances and/or when the sensors do not have a linear response behavior.

SUMMARY OF THE DISCLOSURE

Sensor arrangements according to the present disclosure are configured for analyzing mixtures, including mixtures containing biological substances. The sensor arrangements comprises a substrate, a first reception area for receiving a first material, an electronic component sensor, a test area that is in contact with the electronic component sensor, and a control device. The first reception area and the test area are arranged on the substrate. Further, a control device may be configured for controlling the first reception area and/or the test area so as to move a portion of the first material from the first reception area into the test area.

Methods for operating such sensor arrangements may comprise the steps of providing a first material in the first reception area, of controlling the first reception area and/or the test area so as to move a portion of the first material into the test area, and of detecting a response behavior of the electronic component sensor.

The sensor arrangements and/or methods may be configured for automatically analyzing substances, such as biological substances, in a material.

DETAILED DESCRIPTION

The present disclosure relates to a sensor arrangement for analyzing substances in a material and a method for operating such a sensor arrangement. In particular, the sensor arrangement is configured for analyzing biological substances. FIGS. 1-14 provide examples of sensor arrangements and methods according to the present disclosure. Elements that serve a similar, or at least substantially similar, purpose are labeled with like numbers in each of FIGS. 1-14, and these elements may not be discussed in detail herein with reference to each of FIGS. 1-14. Similarly, all elements may not be labeled in each of FIGS. 1-14, but reference numerals associated therewith may be utilized herein for consistency. Elements, components, steps, and/or features that are discussed herein with reference to one or more of FIGS. 1-14 may be included in and/or utilized with any of FIGS. 1-14 without departing from the scope of the present disclosure.

In the context of the present disclosure, the term "material" can comprise a mixture as well as a pure substance. Unless otherwise indicated, what is to be understood by the term "mixture" in the context of the present disclosure is a material that is comprised of at least two pure substances. Here, the mixture can be homogenous (e.g. a solution) or heterogeneous (e.g. a suspension). In particular, a suspension is a heterogeneous mixture of materials comprising a liquid and solid bodies (particles) distributed therein. An example of a suspension is blood.

As discussed in more detail herein, the present disclosure relates to fluids, such as microfluids. More particularly, the present disclosure relates to sensor arrangements and methods for analyzing biological substances in a material, such as a fluid. The disclosed sensor arrangements and the described methods may be configured such that at least a portion of the first material is moved automatically via the control device. In such sensor arrangements and methods, it is not necessary to manually transport the portion of the first material to the test area, and this may permit a higher number of materials to be analyzed more quickly. The disclosed sensor arrangements and methods may be further configured to permit or provide an in-situ, automatic calibration of the electronic component sensor. Thus, the sensor arrangement can be used for analyzing a substance of a material with an unknown concentration as well as for calibrating the electronic component sensor. This means that the analysis of the substance of the material and the calibration can be performed under the same conditions (e.g. temperature), since these processes can occur within a narrow time frame with respect to each other due to the same sensor arrangement being used. This results in a precise analysis of the substance in the material with the unknown concentration.

Here, the fact that the test area is in contact with the electronic component sensor means that that part of the substance which is located on the test area can be detected and analyzed by the electronic component sensor. In particular, the contact between the test area and the electronic component sensor can be referred to as fluid contact. This means that the test area and the electronic component sensor are in fluid connection with each other. Here, at least one area of the electronic component sensor contacts the test area. Alternatively, the entire electronic component sensor can be arranged on the test area.

A sensor arrangement according to the present disclosure may have a second reception area for receiving a second material and a transporting/mixing area for transporting a portion of the first material and/or a portion of the second material. Further, the transporting/mixing area can be configured to intermix a portion of the first material from the first reception area and a portion of the second material from the second reception area. Here, the second reception area and the transporting/mixing area are arranged on the substrate. Further, the transporting/mixing area is in connection, in particular in direct connection, with the first reception area and/or the second reception area and/or the test area. The control device may be configured for controlling the first reception area and/or the second reception area so as to move a portion of the first material from the first reception area and/or a portion of the second material from the second reception area into the transporting/mixing area. Further, the control device may be configured for controlling the transporting/mixing area so as to move a portion of the second material and/or a mixture of a portion of the first material and a portion of the second material from the transporting/mixing area into the test area. By providing a mixing area or by using the transporting area as a mixing area, a portion of the first material can be intermixed with a portion of the second material in a simple and quick manner. In particular if a pure substance or a material of the same kind as the first material but with a different concentration is provided in the second reception area, different concentrations of the first material or of the second material can be obtained through the mixture in the mixing area. Alternatively, the mixing can be directly performed in the test area, which in some embodiments, may be preferred.

The wording "the same kind" means that the first material and the second material have the same composition with respect to the kind of substance(s) contained therein.

In the context of the present disclosure, if two areas are in connection with each other or in contact with each other, this means that a material exchange between these areas is possible.

Methods according to the present disclosure may comprise the steps of providing a second material in the second reception area, of controlling the first reception area and/or the transporting/mixing area so as to move a portion of the first material from the first reception area into the transporting/mixing area, and of controlling the second reception area and/or the transporting/mixing area so as to move a portion of the second material from the second reception area into the transporting/mixing area. Further, the methods may comprise the step of mixing the portion of the first material with the portion of the second material, of controlling the transporting/mixing area and/or the test area so as to move the mixture of the portion of the first material and the portion of the second material into the test area. Subsequently, a response behavior of the electronic component sensor may be detected.

Sensor arrangements according to the present disclosure may comprise a third reception area for receiving a portion of the first material and/or a portion of the second material and/or a mixture of a portion of the first material and a portion of the second material. When present, the third reception area is arranged on the substrate, and is in connection with the transporting/mixing area and/or the test area. The control device thus may be configured for controlling the test area and/or the third reception area so as to move a portion of the first material and/or a portion of the second material and/or a mixture of a portion of the first material and a portion of the second material from the test area and/or the transporting/mixing area into the third reception area. The third reception area can serve as a waste reservoir. In particular, the third reception area can be in direct connection with the transporting/mixing area and/or the test area.

Further, sensor arrangements according to the present disclosure may comprise a fourth reception area that is configured for receiving a third material. When present, the fourth reception area is arranged on the substrate and is in connection with the transporting/mixing area and/or with the test area. In particular, the fourth reception area can be in direct connection with the transporting/mixing area and/or the test area.

The first reception area and/or the second reception area and/or the third reception area and/or the fourth reception area and/or the transporting/mixing area and/or the test area and/or the control device may be electrically conducting. Thus, the described areas as well as the control device may be embodied to be electrically conducting in such a manner that the first material, the second material, the mixture of the first material and the second material or the third material can be moved by applying an electrical voltage to the areas. The first reception area and/or the second reception area and/or the third reception area and/or the transporting/mixing area and/or the test area and/or the control device in particular may be embodied as electrodes. By applying an electrical voltage, an electrical field is generated through which the first material, the second material, the mixture of the first material and the second material or the third material, which are electrically charged, are moved. The first reception area and/or the second reception area and/or the third reception area and/or the fourth reception area and/or the transporting/mixing area and/or the test area and/or the control device may have a specific electrical resistance of $10^{-6}$ ($\Omega$cm), wherein the first reception area and/or the second reception area and/or the third reception area and/or the fourth reception area and/or the transporting/mixing area and/or the test area and/or the control device are embodied as metal films. Possible metals may, for example, be copper, gold, chrome, or silver.

The first reception area and/or the second reception area and/or the third reception area and/or the fourth reception area and/or the transporting/mixing area and/or the test area and or the control device can also be formed as thin layer from a nanomaterial, such as e.g. nanotubes and/or nanoparticles of conducting polymers, and can have a specific electric resistance of between $10^{2}$ $\Omega cm$ and $10^{-2}$ $\Omega cm$.

The transporting/mixing area may be formed by a plurality of individual subareas, and the control device may be configured for controlling each subarea separately. In this way, for one thing, the parallel transportation of different portions of the first material and/or of the second material and, for another thing, a better mixing of a portion of the first material with a portion of the second material is facilitated by moving them through the individual subareas.

The electronic component sensor has a detection area that is advantageously arranged on the test area.

The first reception area and/or the second reception area and/or the third reception area and/or the fourth reception area are configured for receiving a fluid.

The transporting/mixing area may be controlled in such a manner that the mixture of the portion of the first material and the portion of the second material is separated into a first part of the mixture and a second part of the mixture. The transporting/mixing area and/or the test area further may be controlled in such a manner that the first part of the mixture is moved into the test area for detecting a response behavior of the electronic component sensor, and that the second part of the mixture remains in the transporting/mixing area. Further, the first reception area and/or the transporting/mixing area may be controlled so as to move a further portion of the first material from the first reception area into the transporting/mixing area, in which the further portion of the first material is intermixed with the second part of the mixture. The test area and/or the third reception area may be controlled so as to move the first part of the mixture into the third reception area. Further, the transporting/mixing area and/or the test area may be controlled in such a manner that the second part of the mixture which is intermixed with the further portion of the first material is moved from the transporting/mixing area into the test area for detecting a response behavior of the electronic component sensor. This control may be performed the control device and/or by methods according to the present disclosure.

The previously described examples of steps of separating the substance present in the transporting/mixing area into two parts, of moving the one part into the test area, of retaining the other part in the transporting/mixing area, and of the renewed mixing of the other part with a further portion of the first material can be repeated for creating a characteristic curve of the electronic component sensor. This means that the second part of the mixture that is intermixed with the further portion of the first material can be separated again into two parts instead of being moved directly into the test area. Here, the one part is brought into the test area for detecting the response behavior and is subsequently moved into the third reception area, with the other part being mixed with yet another further portion of the first material. The method can be repeated until there is no more first material present in the first reception area.

In other words, for generating the characteristic curve of the electronic component sensor, the substance that is present in the transporting/mixing area at any point in time may be separated into two parts, of which the one part is transported into the test area and the other is again intermixed with a/another portion of the first material in the transporting/mixing area. In the first mixture, the material present in the transporting/mixing area corresponds to a first mixture of a portion of the first material and a portion of the second material. In the second mixture, the material present in the transporting/mixing area corresponds to a mixture of a part of the mixture of the first mixture and a portion of the first material, etc.

Put in general terms, in the second mixture and each subsequent mixture of the material that is present in the transporting/mixing area corresponds to a mixture of a part of the mixture that is created by the previous separation and a portion of the first material.

The material that is present at any point in time in the transporting/mixing area can either be separated into different parts or into identical (same size) parts, namely divided in half.

Here, the term "mixture" refers to the result of a mixture of two substances, independently of whether the substances are pure substances or are themselves mixtures.

The first material may be a diluent or a dilution solution, and the second material may be a mixture of the same dilution solution or the same diluent with a substance to be analyzed. Thus, a mixture with a different concentration of the substance to be analyzed can be obtained in every mixing procedure.

A control device may be provided and configured for controlling the electrodes of the control device so as to move the first material and/or the second material and/or the third material and/or a mixture of the first material and the second material. The control device can be any programmable unit, such as for example a computer, an embedded micro controller system, FPGA or ASIC.

Further, the present disclosure relates to a computer program, comprising instructions that cause the previously described sensor arrangement to perform the method steps of the previously described method.

Further, the present disclosure relates to a computer-readable medium on which the computer program is saved. The control device may be configured to implement, or execute the steps of, the computer program.

The electronic component sensor may be configured to detect biological substances such as, for example, glucose, lactate, $Na^+$, $K^+$, $Ca^{2+}$, $NH4^+$, $Cl^-$, dopamine, acetylcholine, histamine, DNA and their concentration in a material, e.g. in a mixture.

The electronic component sensor may be a transistor sensor. Another example type of sensor that can be used as the electronic component sensor may, for example, be a SAW sensor ("surface acoustic wave sensor").

An example of a sensor arrangement 1 according to a first embodiment of the present disclosure is described in detail by referring to FIGS. 1 to 4.

Figure 1:
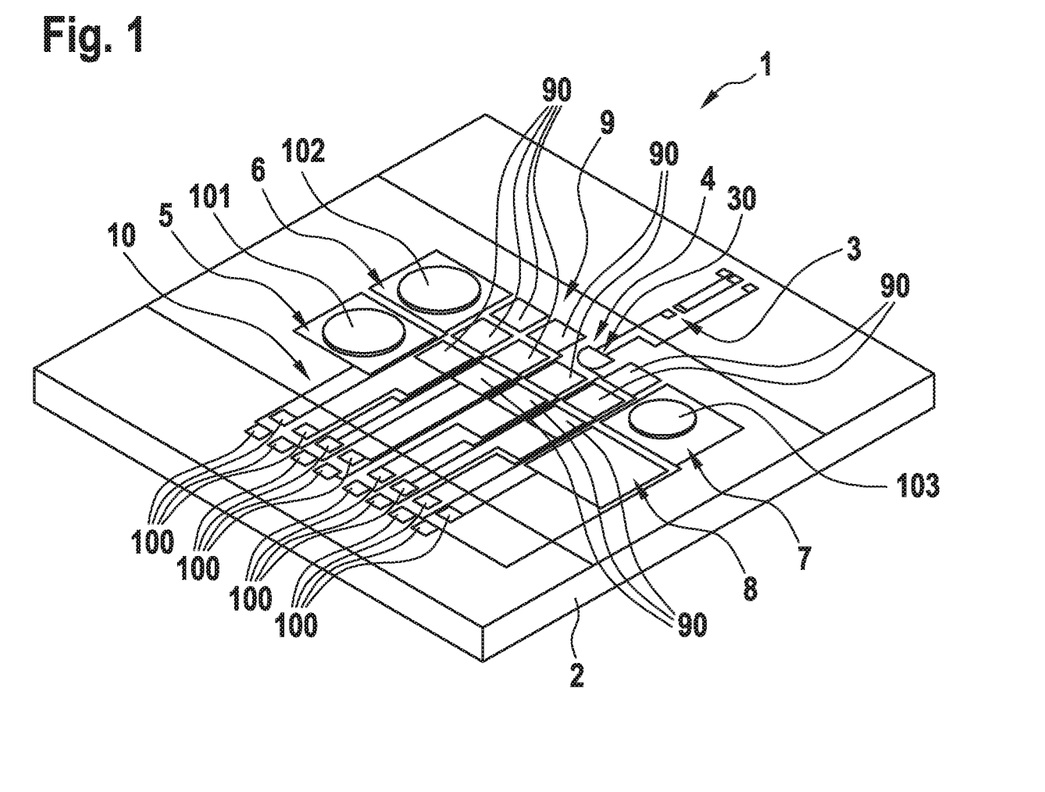
FIG. 1 is a schematically simplified perspective view of a sensor arrangement according to a first embodiment of the present disclosure.

As can be seen in FIG. 1, the sensor arrangement 1 has a substrate 2, an electronic component sensor that is embodied as a transistor sensor 3, and a test area 4 that is in contact with the transistor sensor 3.

The substrate 2 serves mainly as a support structure for supporting the other components of the sensor arrangement 1 and is formed of an electrically insulating material. Further, the substrate 2 can be embodied to be rigid or bend-proof (e.g., from glass), or to be flexible or elastic (e.g., from a plastic material, paper etc.). Alternatively, the substrate 2 can be made of a bendable material in some sections and from a bend-proof material in others. The substrate 2 may be formed as a foil and may be made at least partially from a transparent material such as glass or a transparent polymer.

The test area 4 is arranged on the substrate 2. In the sensor arrangement 1 shown in FIG. 1, the substrate 2 is illustrated as including a first reception area 5 for receiving a first material, a second reception area 6 for receiving a second material, a third reception area 7 and a fourth reception area 8. These reception areas may be described as being provided on the substrate 2.

In general, the reception areas 5 to 8 are respectively configured for receiving a material or substance.

The first material can be a dilution solution (buffer solution) 101 or a diluent, for example water, and the second material can be a standard solution 102 with a known concentration (e.g. glucose solution, i.e. a solution of water and glucose).

Further, the sensor arrangement 1 comprises a transporting area 9 that is configured for transporting at least a portion of the first material from the first reception area 5 and/or at least a portion of the second material from the second reception area 6. The transporting area 9 additionally serves as a mixing area that is configured for mixing a portion of the first material with a portion of the second material.

The transporting/mixing area 9 is arranged on the substrate 2 and is in direct connection with the first reception area 5, the second reception area 6 and the test area 4. In particular, the transporting/mixing area 9 is formed from a plurality of individual subareas 90.

The third reception area 7 is configured for receiving a portion of the first material and/or a portion of the second material and/or a mixture of a portion of the first material and a portion of the second material. Further, the third reception area 7 is in connection with the transporting/mixing area 9 and the test area 4. In particular, the third reception area 7 directly communicates with the transporting/mixing area 9.

The fourth reception area 8 is configured for receiving a third material and is in direct connection with the transporting/mixing area 9. The third material can be a test solution of the same kind as the standard solution with an unknown concentration.

As for the spatial arrangement, the transporting/mixing area 9 is located between the first reception area 5, the second reception area 6, the third reception area 7, and the fourth reception area 8.

Further, the first reception area 5, the second reception area 6, the third reception area 7, the fourth reception area 8, the transporting/mixing area 9, and the test area 4 are electrically conducting. In particular, the first reception area 5, the second reception area 6, the third reception area 7, the fourth reception area 8, the transporting/mixing area 9 and the test area 4 are embodied as electrodes.

The first reception area 5, the second reception area 6, the third reception area 7, and the fourth reception area 8 each respectively have a surface that is larger than the surface of a subarea 90, and are advantageously arranged on an edge area of the substrate 2.

As shown, a control device 10 may be provided in the sensor arrangement 1.

The control device 10 is configured for controlling the first reception area 5 and/or the test area 4 so to move a portion of the first material from the first reception area 5 into the test area 4.

Further, the control device 10 is configured for controlling the first reception area 5 and/or the second reception area 6 and/or the transporting/mixing area 9 so as to move a portion of the first material from the first reception area 5 and/or a portion of the second material from the second reception area 6 into the transporting/mixing area 9, and/or to move a portion of the second material and/or a mixture of a portion of the first material and a portion of the second material from the transporting/mixing area 9 into the test area 4.

Further, the control device 10 is configured for controlling the test area 4 and/or the third reception area 7 so as to move a portion of the first material and/or a portion of the second material and/or a mixture of a portion of the first material and a portion of the second material from the test area 4 and/or the transporting/mixing area 9 into the third reception area 7.

In particular, the control device 10 comprises a plurality of control elements 100, wherein the test area 4, the first reception area 5, the second reception area 6, the third reception area 7, and the fourth reception area 8 each can be controlled by one of the control elements 100. Each subarea 90 of the transporting/mixing area 9 can be separately controlled by one control element 100.

In other words, the number of the control elements 100 corresponds to the number of the sum of the test area 4, the first reception area 5, the second reception area 6, the third reception area 7, the fourth reception area 8 and the subareas 90 of the transporting/mixing area 9.

The control elements 100 of the control device 10 may be embodied to be electrically conducting, such as by being embodied as electrodes.

The transistor sensor 3 has a detection area 30 that is arranged on the test area 4. In particular, the transistor sensor 3 is embodied as a EGFET (extended gate field effect transistor).

Figure 3:
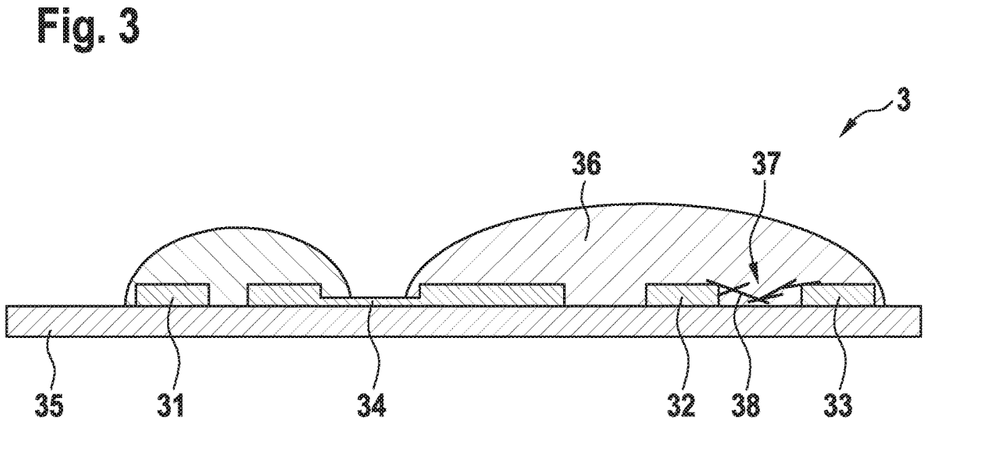
FIG. 3 is a schematically simplified sectional view of a transistor sensor of the sensor arrangement of FIG. 1.
Figure 4:
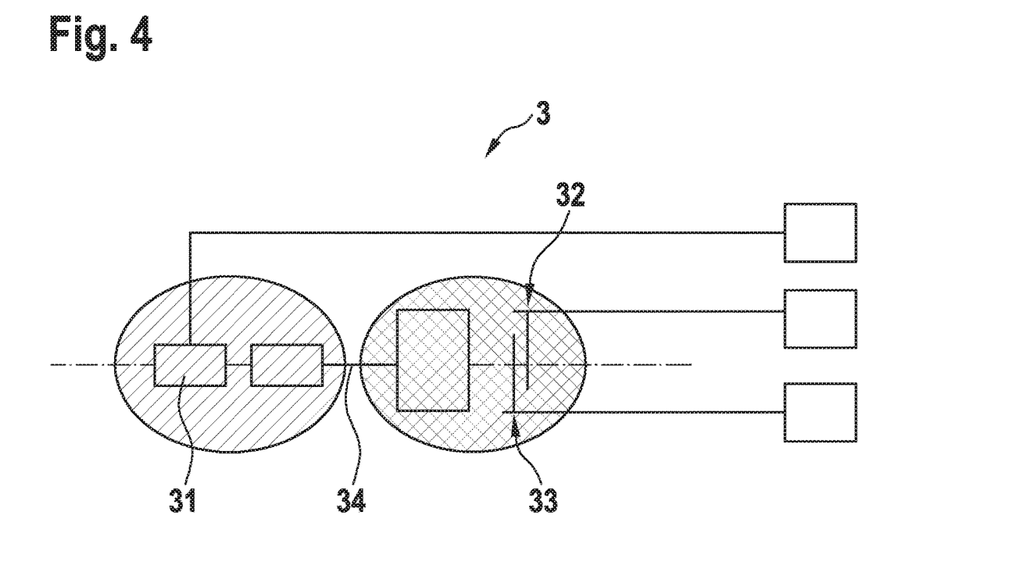
FIG. 4 is a schematically simplified top view of the transistor sensor of FIG. 3.

As can be seen in FIGS. 3 and 4, the transistor sensor 3 has a gate electrode 31, a drain electrode 32, a source electrode 33 and a floating gate electrode 34 that are arranged on a transistor substrate 35. The gate electrode 31 and the floating gate electrode 34 are located on a test area 4 of the sensor arrangement 1 and can be covered by the material to be analyzed, wherein the drain electrode 32 and the source electrode 33 are arranged outside the test area 4 and are covered by an electrolyte 36. A semiconductor channel 37 of carbon nanotubes (CNTs) 38 is formed between the drain electrode 32 and the source electrode 33. The gate electrode 31 and the floating gate electrode 34 correspond to the detection area 30.

Figure 2:
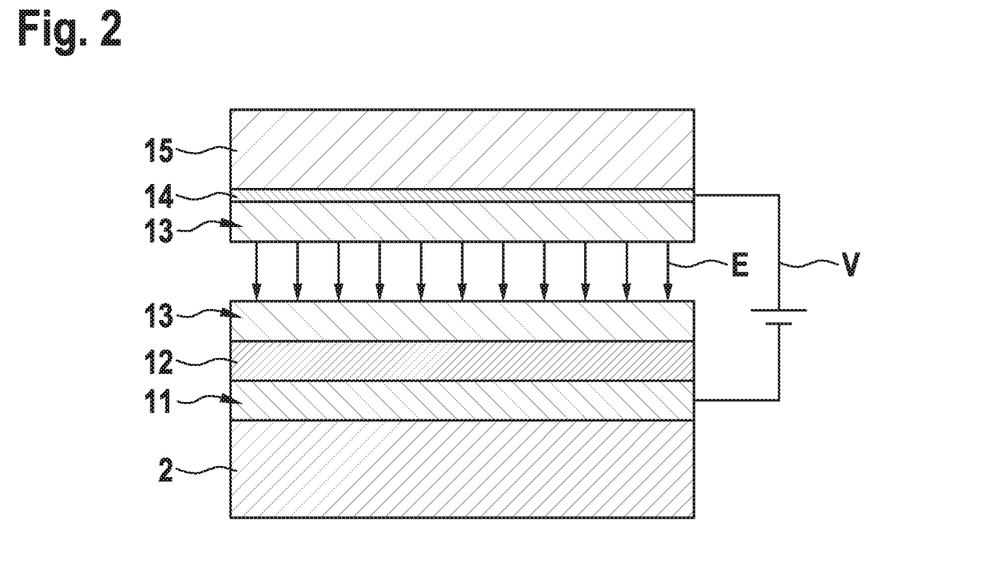
FIG. 2 is a schematically simplified sectional view of the sensor arrangement of FIG. 1.

FIG. 2 shows a schematically simplified sectional view of the sensor arrangement 1 of FIG. 1.

For the purpose of simplification, in FIG. 2 the first reception area 5, the second reception area 6, the third reception area 7, the fourth reception area 8, the test area 4 and the transporting/mixing area 9 are shown as a single area 11. Applied to the area 11 is an insulating layer 12 that is configured for electrically insulating the area 11. A hydrophobic film 13 is arranged on the insulating layer 12, separated from a support element 15 through an electrically conducting layer 14. In this case, the hydrophobic film 13 has two layers. However, it is also possible that the hydrophobic film 13 has only one layer or has multiple layers. The hydrophobic film 13 serves for electrical insulation between the area 11 and the substance to be analyzed. The electrically conducting layer 14 can for example be formed of indium tin oxide (ITO;) or a film of silver nanowires, wherein the support element 15 may be made of glass, plastic material or polyimide. The first reception area 5, the second reception area 6, the third reception area 7, the fourth reception area 8, the test area 4, and the transporting/mixing area 9 may be made of metal. However, other materials are may be used, such as for example silver nanowires, indium tin oxide, or a nanoparticulate film.

To move a portion of the first material, a portion of the second material, a portion of the third material or a mixture of a portion of the first material and a portion of the second material, an electrical voltage V may be applied between the electrically conducting layer 14 and the area 11. In this manner, an electrical field E can be generated, whereby a material arranged on one sublayer of the hydrophobic film 13 can be moved. Thus, a portion of the first material, a portion of the second material, a portion of the third material, or a mixture of a portion of the first material and a portion of the second material can be moved from one area to another area. The electrical field E is perpendicular to the plane of the area 11, or is vertical if the substrate 2 or a surface of the substrate 2 on which the area 11 is formed is positioned horizontally. The described kind of manipulation of materials is based on the EWOD principle (electrowetting; electrowetting-on-dielectric).

For those components of the present disclosure that have an electrically insulating function, polyvinyl chloride (foil), polyethylene (foil), polycarbonate (substrate), glass, and/or ceramic (foil) can be used, for example. In particular, the components of the present disclosure with an insulating function may have a specific electric resistance in the range of between $10^2 \ \Omega cm$ and $10^{16} \ \Omega cm$.

In the present disclosure, a difference between a specific electric resistance of an electrically conducting component and that of an electrically insulating component may be in the order of magnitude of $10^6$ or higher. This means that a ratio of a specific electric resistance of an electrically conducting component to that of an electrically insulating component is greater than or equal to $10^6$.

In the following, methods for operating the sensor arrangement 1 according to the first embodiment of the present disclosure are described with reference to FIGS. 5 to 9.

Figure 5:
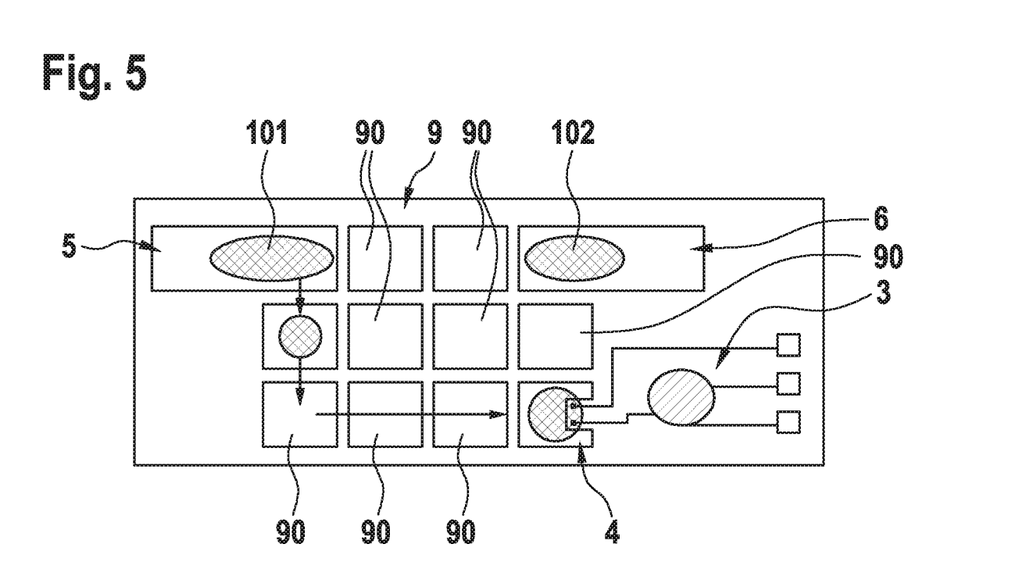
FIG. 5 to FIG. 9 are schematic views of the sensor arrangement according to FIG. 1 illustrating steps of a method according to the present disclosure for operating the sensor arrangement.
Figure 6:
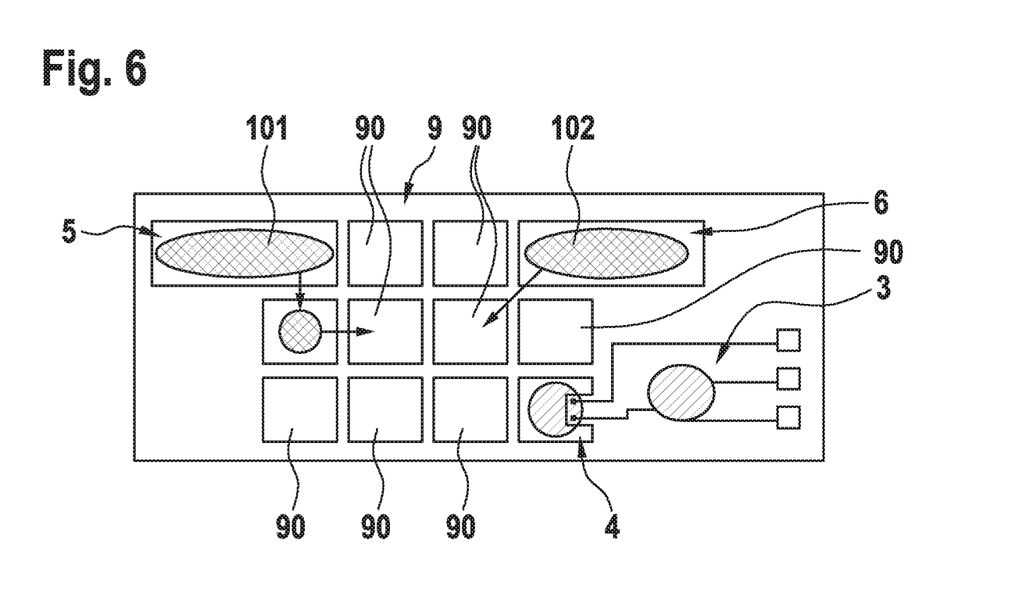

A first material is introduced into the first reception area 5 and a second material is introduced into the second reception area 6. As has already been described, the first material can be a dilution solution (buffer solution) 101 or a diluent, for example water, and the second material can be a standard solution 102 with a known concentration.

At first, a predefined portion, e.g. a drop, of the first material is moved from the first reception area 5 to the test area 4 (FIG. 5). For this purpose, the first reception area 5 and/or the transporting/mixing area 9 and/or the test area 4 is controlled via the control device 10.

Figure 10:
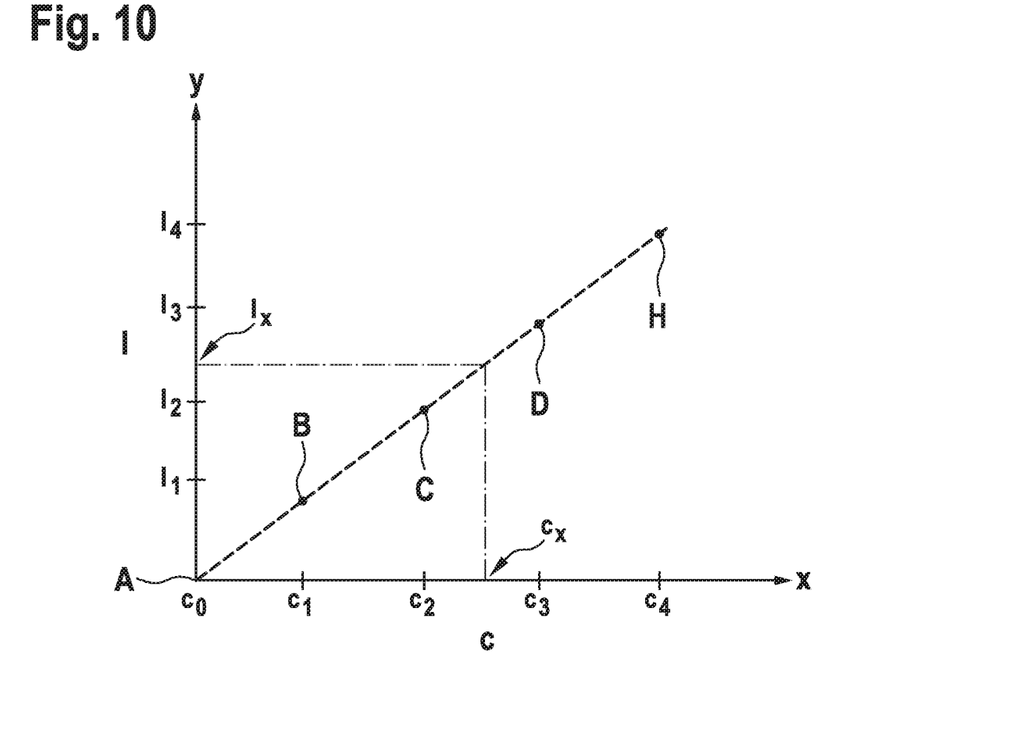
FIG. 10 is a rendering of a characteristic curve of the transistor sensor.

Subsequently, the response behavior of the transistor sensor 3 is detected by applying a voltage to the transistor sensor 3. In particular, a current flowing through the transistor sensor 3 is measured. Thus, the point A of the characteristic curve of the transistor sensor 3 shown in FIG. 10 is determined. The x-axis of the diagram of FIG. 10 corresponds to the concentration of a solution of a substance to be analyzed, wherein the y-axis indicates the measured current flowing through the transistor sensor 3.

After the response behavior of the transistor sensor 3 has been determined, the predefined portion of the first material is moved to the third reception area (waste reservoir) 7 by controlling the test area 4 and/or the third reception area 7.

Subsequently, the first reception area 5 and/or the transporting/mixing area 9 are controlled via the corresponding control elements 100 of the control device 10 (FIG. 6) so as to move a predefined portion of the first material from the first reception area 5 into the transporting and/or mixing area 9.

Accordingly, the second reception area 6 and/or the transporting/mixing area 9 are controlled via the respective control elements 100 of the control device 10 (FIG. 6) so as to move a predefined portion of the second material from the second reception area 6 into the transporting/mixing area 9.

Figure 7:
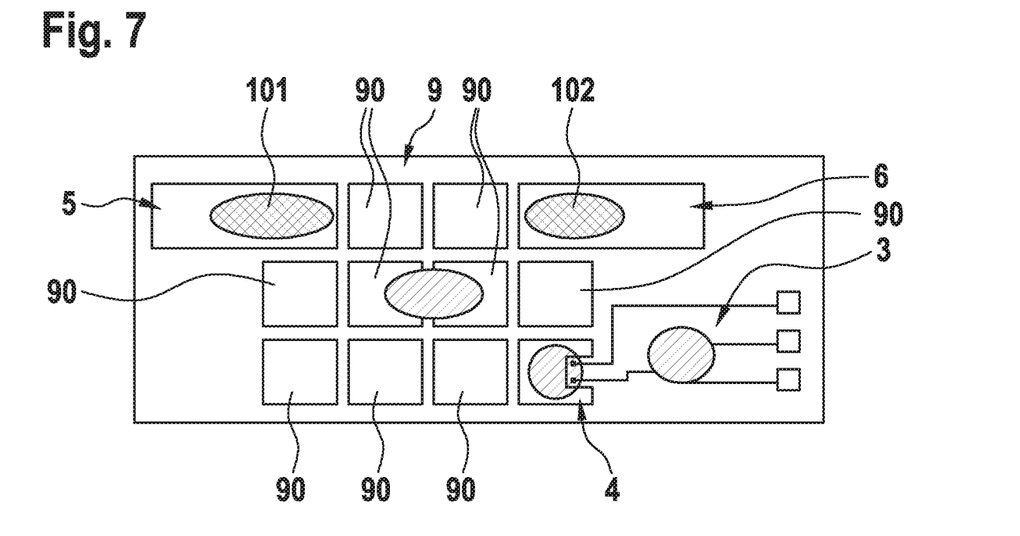

In the transporting/mixing area 9, the predefined portion of the first material is intermixed with the predefined portion of the second material (FIG. 7). For thorough intermixing, the mixture of the portion of the first material and the portion of the second material may be moved through the subareas 90 in the transporting/mixing area 9 multiple times.

Figure 8:
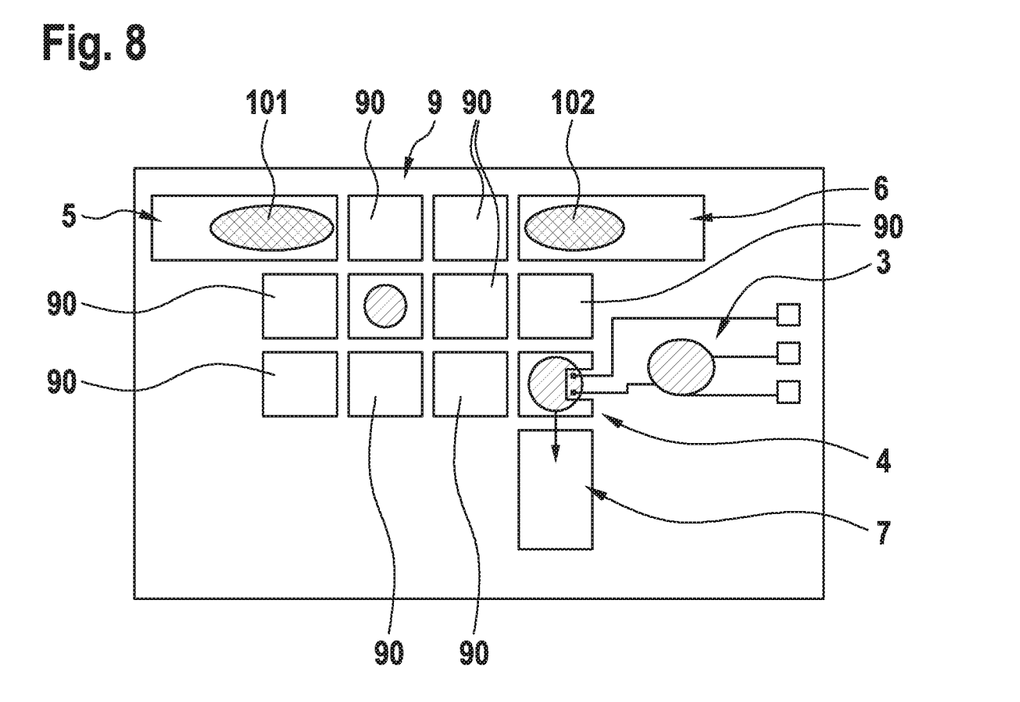

Subsequently, the mixture of the portion of the first material and the portion of the second material is separated into a first part of the mixture and a second part of the mixture by controlling the transporting/mixing area 9 (FIG. 8). Then, the transporting/mixing area 9 and/or the test area 4 is controlled in such a manner that the first part of the mixture is moved into the test area 4 for detecting the response behavior of the transistor sensor 3, and the second part of the mixture remains in the transporting/mixing area 9.

After the response behavior of the transistor sensor 3 has been detected, the first part of the mixture is moved to the third reception area 7.

It is to be understood that the first part of the mixture and the second part of the mixture do not have to be of the same size. In other words, the mixture does not have to be divided in half in order to create the first part of the mixture and the second part of the mixture.

Then, the first reception area 5 and/or the transporting/mixing area 9 are controlled so as to move a further portion of the first material from the first reception area 5 into the transporting/mixing area 9. In the transporting/mixing area 9, the further portion of the first material is intermixed with the second part of the mixture.

The new mixture of the further portion of the first material and the second part of the mixture from the separation of the first mixture is again divided into two parts of the mixture, and the previously described method is repeated until the points of, or defining, the characteristic curve are determined. For example, in FIG. 10, characteristic points B, C, D, and H are shown. It is to be understood that the obtained characteristic curve of the transistor sensor 3 is more precise if mixtures of different concentrations are analyzed by means of the transistor sensor 3 by repeated dilution of the resulting mixture.

The above-described method corresponds to a calibration of the transistor sensor 3. The characteristic curve shown in FIG. 10 then corresponds to a calibration curve of the transistor sensor 3.

Figure 9:
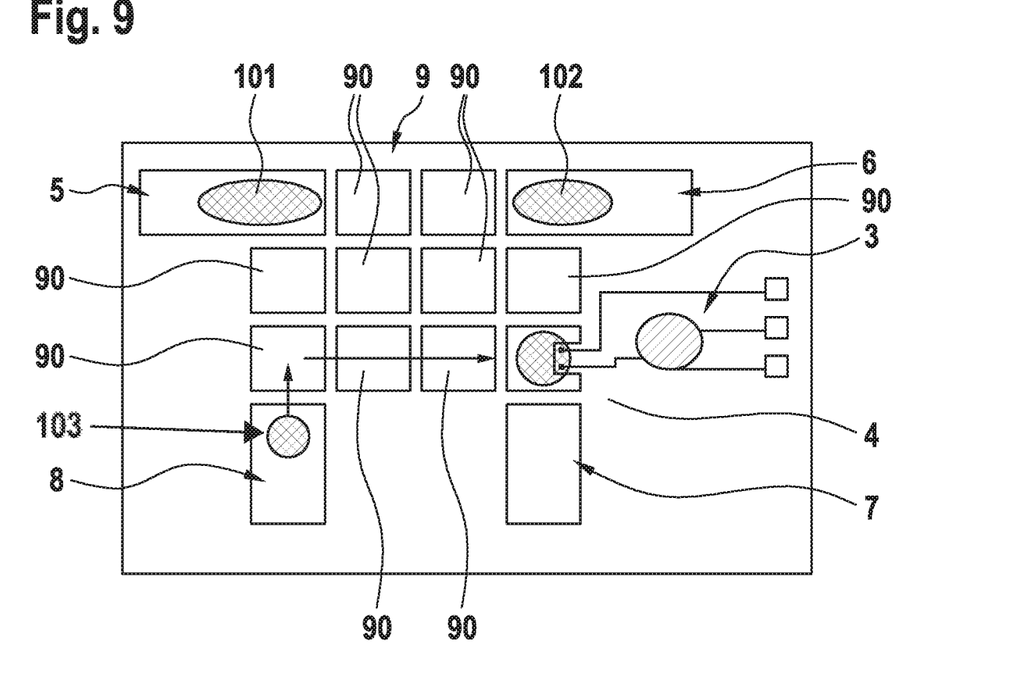

Subsequently, and as illustrated in FIG. 9, a third material can be analyzed by means of the transistor sensor 3. The third material can be a test solution 103 with an unknown concentration of the substance to be analyzed (e.g. a glucose solution).

For this purpose, a portion of the third material, which is provided in the fourth reception area 8, can be moved to the test area 4 by controlling the fourth reception area 8 and/or the transporting/mixing area 9 and/or the test area 4.

Here, the response behavior or the current $I_x$ flowing through the transistor sensor 3 is measured. Then, the concentration $c_x$ that corresponds to the current $I_x$ is determined based on the characteristic curve of FIG. 10. Thus, the concentration of the third material can be determined.

Figure 14:
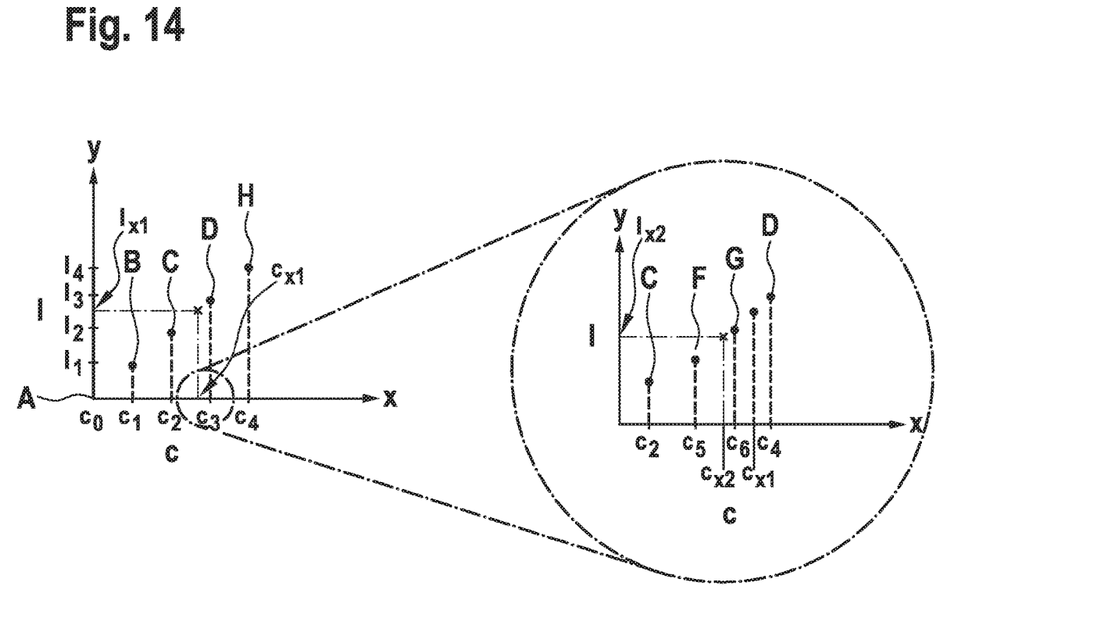
FIG. 14 is a further rendering of a characteristic curve of a transistor sensor according to the present disclosure.

After the value of the unknown concentration $c_x$ of the third material has been calculated, the method for creating a characteristic curve of the transistor sensor 3 can be repeated by performing a calibration by the calculated value of the concentration $c_x$. In other words, the determined value is used as a starting point or a first value $c_{x1}$ for the new calibration. This is shown in FIG. 14. The left side of FIG. 14 essentially shows the characteristic curve of FIG. 10, with the right side showing an enlarged rendering of an area of this characteristic curve comprising the result of the renewed calibration.

In the area of the first value $c_{x1}$, the calibration curve has further points F, G with the concentrations C5, C6. Points F, G are located between points C and D, which have been determined according to the first calibration. Thus, in the area of the first determined value, the generated calibration curve is more closely approximated to the actual characteristic curve of the transistor sensor 3, whereby the precision of the calculation of the concentration $c_x$ of the third material is increased. Since the calibration curve has more points due to the repetition of the method in the area of the first determined value $c_{x1}$ or by the first determined value $c_{x1}$, an even more precise second value $c_{x2}$ for the concentration $c_x$ of the third material can be determined. In the shown case, the second value $c_{x2}$ is for example smaller than the first determined value $c_{x1}$ and lies between the concentrations c5, c6. Here, the first determined value $c_{x1}$ of the concentration $c_x$ of the third material as determined according to the first calibration can be understood as an estimate of the concentration, which is defined more precisely through the new (second) calibration.

In the new calibration, the portions of the first material and the second material for creating a mixture are selected based on the first determined value $c_{x1}$ in such a manner that the mixture created in the first step of the new calibration is in the range of the first value $c_{x1}$ with respect to its concentration. Correspondingly, the portion of the resulting mixture and the portion of the first material, which are mixed with each other in the second step, can be selected in such a manner that the concentration of the newly created mixture also lies in the range of the first value $c_{x1}$.

In other words, the portions of the materials that are to be intermixed are selected in such a manner that a material or mixture that is present at any point in time in the transporting/mixing area 9 has a concentration that is in the range of the first determined value $c_{x1}$. The second calibration is advantageously performed in a concentration range about the first determined value $c_{x1}$, which is smaller than the concentration range in which the first calibration occurs.

Performing a second calibration of the transistor sensor 3 based on a value of an unknown concentration of the third material as determined based on a first calibration may be particularly advantageous in sensors that do not have a linear response behavior.

The sensor arrangement 1 and methods according to the present disclosure thus may enable the calibration of the transistor sensor 3 and the analysis of materials to be performed on site quickly and without a time lag with respect to each other. Further, an extremely small test volume may be necessary for calibrating the transistor sensor 3 in sensor arrangement 1.

Figure 11:
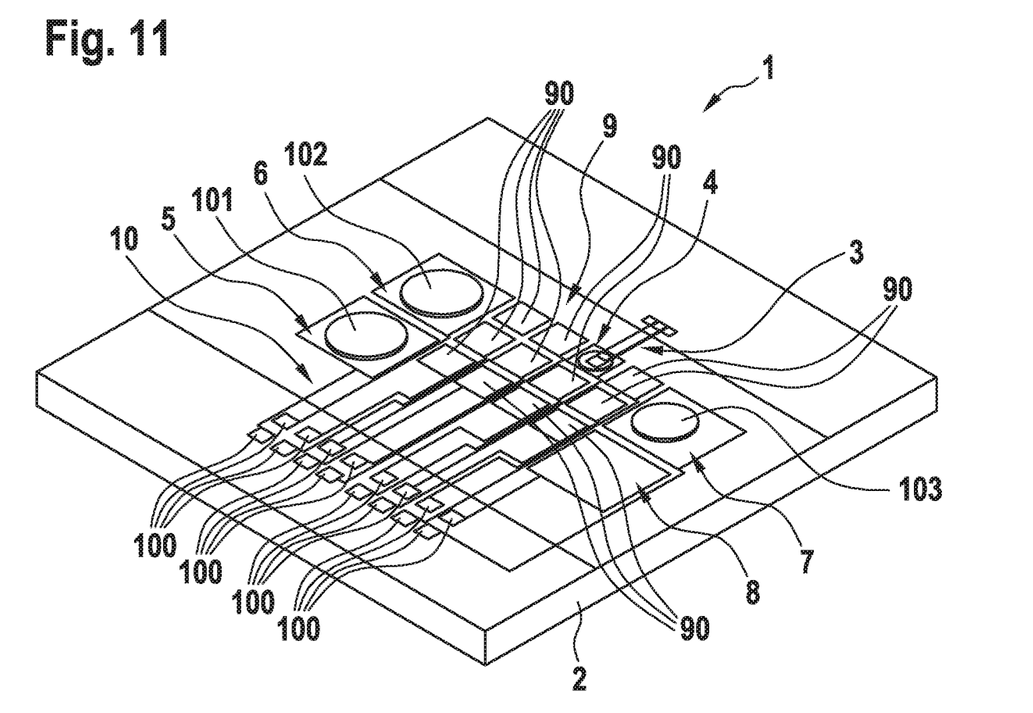
FIG. 11 is a schematically simplified perspective view of a sensor arrangement according to a second embodiment of the present disclosure.
Figure 12:
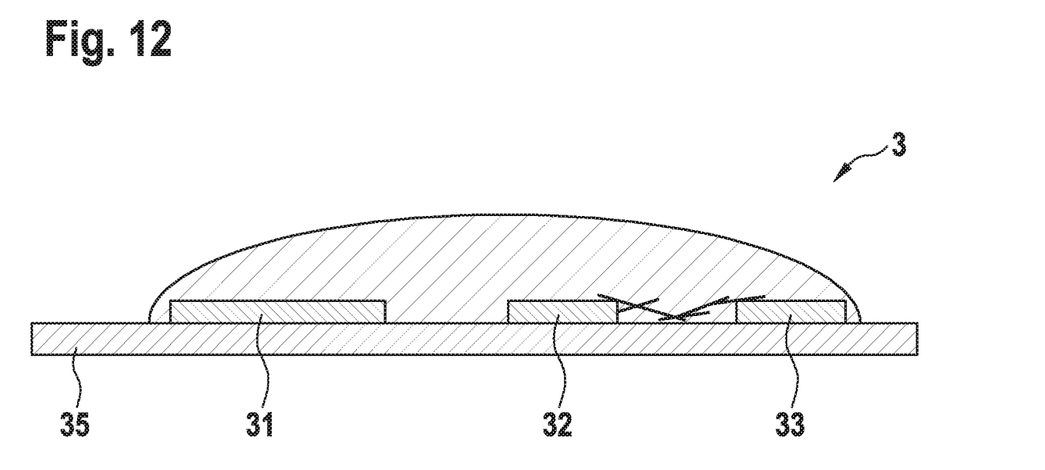
FIG. 12 is a schematically simplified sectional view of a transistor sensor of the sensor arrangement according to FIG. 11.
Figure 13:
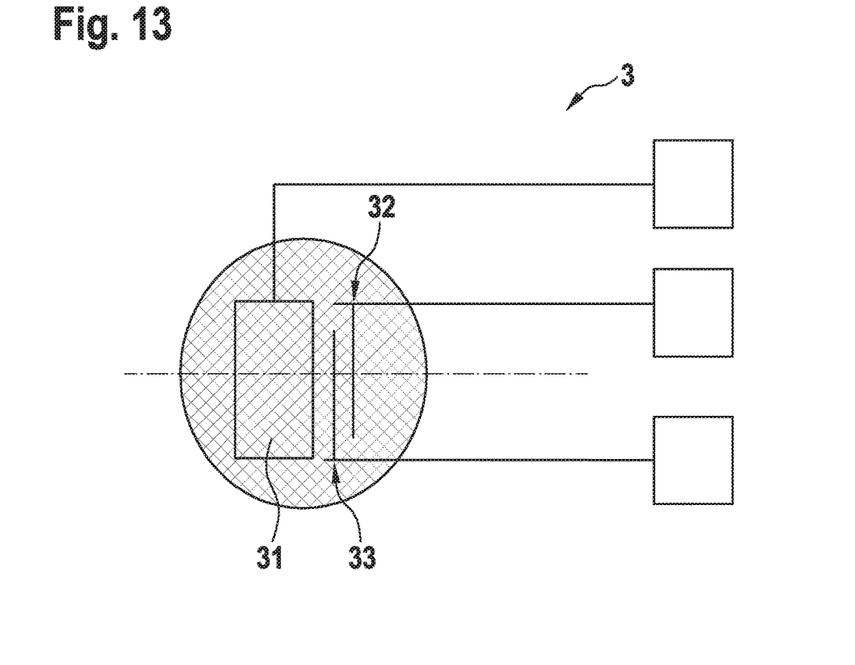
FIG. 13 is a schematically simplified top view of the transistor sensor of FIG. 12.

FIGS. 11 to 13 show a sensor arrangement 1 according to a second embodiment of the present disclosure.

The sensor arrangement 1 according to the embodiment of FIGS. 11-13 generally differs from the sensor arrangement 1 of FIGS. 1-9 in that, in the sensor arrangement of FIGS. 11-13, the transistor sensor 3 has no floating gate electrode and is completely arranged on the test area 4. In other words, the gate electrode 31, the drain electrode 32 and the source electrode 33 are located within the test area 4.

As FIG. 11 shows, the rest of the structure of the sensor arrangement 1 is identical to that of the sensor arrangement 1 of FIGS. 1-10.

FIGS. 12 and 13 show views of the transistor sensor 3 according to the second embodiment.

In addition to the above written description of the present disclosure, the drawn renderings of the present disclosure of FIGS. 1 to 14 are herewith explicitly referred to for an additional disclosure of the present disclosure.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

PARTS LIST 1 sensor arrangement
2 substrate
3 electronic component sensor (transistor sensor)
4 test area
5 first reception area
6 second reception area
7 third reception area
8 fourth reception area
9 transporting/mixing area
10 control device
11 area
12 insulating layer
13 hydrophobic film
14 electrically conducting layer
15 support element
30 detection area
31 gate electrode
32 drain electrode
33 source electrode
34 floating gate electrode
35 transistor substrate
36 electrolyte
37 semiconductor channel
38 carbon nanotube
90 subarea
100 control element
101 dilution solution
102 standard solution
103 test solution
A point
B point
C point
D point
E electrical field
F point
G point
H point
$c_x$ unknown concentration
$c_{x1}$ first value
$c_{x2}$ second value
$c_1$-$c_6$ concentrations
$I_x$ current

The invention claimed is:

1. A sensor arrangement (1) for analyzing substances in a material, the sensor arrangement comprising:
a substrate (2),
a first reception area (5) for receiving a first material,
an electronic component sensor (3),
a test area (4) that is in contact with the electronic component sensor (3),
a control device (10),
a second reception area (6) for receiving a second material, and
a transporting/mixing area (9) for at least one of (i) transporting at least one of a portion of the first material or a portion of the second material, or (ii) mixing a portion of the first material with a portion of the second material,
wherein the first reception area (5) and the test area (4) are arranged on the substrate (2),
wherein the control device (10) is configured for controlling at least one of the first reception area (5) or the test area (4) to move a portion of the first material from the first reception area (5) into the test area (4),
wherein the second reception area (6) and the transporting/mixing area (9) are arranged on the substrate, and the transporting/mixing area (9) is in connection with at least one of the first reception area (5), the second reception area (6), or the test area (4), and
wherein the control device (10) is configured for controlling at least one of (i) the first reception area (5), (ii) the second reception area (6), or (iii) the transporting/mixing area (9) to at least one of (a) move at least one of a portion of the first material from the first reception area (5) or a portion of the second material from the second reception area (6) into the transporting/mixing area (9), or (b) move at least one of a portion of the second material or a mixture of a portion of the first material and a portion of the second material from the transporting/mixing area (9) into the test area (4).

2. The sensor arrangement (1) according to claim 1, further comprising:
a third reception area (7) for receiving at least one of (i) a portion of the first material, (ii) a portion of the second material, or (iii) a mixture of a portion of the first material and a portion of the second material, wherein the third reception area (7) is arranged on the substrate (2), and is in connection with at least one of the transporting/mixing area (9) or the test area (4), and wherein the control device (10) is configured for controlling at least one of the test area (4) or the third reception area (7) to move at least one of (i) a portion of the first material, (ii) a portion of the second material, or (iii) a mixture of a portion of the first material and a portion of the second material from at least one of the test area (4) or the transporting/mixing area (9) into the third reception area (7).

3. The sensor arrangement (1) according to claim 2, wherein at least one of the first reception area (5), the second reception area (6), the third reception area (7), the transporting/mixing area (9), the test area (4), or the control device (10) are electrically conducting, in particular being embodied as electrodes.

4. The sensor arrangement (1) according to claim 1, wherein the transporting/mixing area (9) is formed of a plurality of individual subareas (90), and further wherein the control device (10) is configured for separately controlling each subarea (90).

5. The sensor arrangement (1) according to claim 2, wherein the transporting/mixing area (9) is formed of a plurality of individual subareas (90), and further wherein the control device (10) is configured for separately controlling each subarea (90).

6. The sensor arrangement (1) according to claim 3, wherein the transporting/mixing area (9) is formed of a plurality of individual subareas (90), and further wherein the control device (10) is configured for separately controlling each subarea (90).

7. The sensor arrangement (1) according to claim 1, wherein the electronic component sensor (3) has a detection area (30) that is arranged on the test area (4).

8. A method for operating the sensor arrangement (1) according to claim 1, comprising the steps of:
providing a first material in the first reception area (5),
controlling at least one of the first reception area (5) or the test area (4) so as to move a portion of the first material into the test area (4), and
detecting a response behavior of the electronic component sensor (3).

9. The method according to claim 8, comprising the steps of:
providing a second material in the second reception area (6),
controlling at least one of the first reception area (5) or the transporting/mixing area (9) so as to move a portion of the first material from the first reception area (5) into the transporting/mixing area (9),
controlling at least one of the second reception area (6) or the transporting/mixing area (9) so as to move a portion of the second material from the second reception area (6) into the transporting/mixing area (9),
mixing the portion of the first material with the portion of the second material,
controlling at least one of the transporting/mixing area (9) or the test area (4) so as to move the mixture of the portion of the first material and the portion of the second material into the test area (4), and
detecting the response behavior of the electronic component sensor (3).

10. The method according to claim 9, comprising the steps of:
controlling the transporting/mixing area (9) in such a manner that the mixture of the portion of the first material and the portion of the second material is separated into a first part of the mixture and a second part of the mixture,
controlling at least one of the transporting/mixing area (9) or the test area (4) in such a manner that the first part of the mixture is moved into the test area (4) for detecting a response behavior of the electronic component sensor (3), and the second part of the mixture remains in the transporting/mixing area (9),
controlling at least one of the first reception area (5) or the transporting/mixing area (9) so as to move a further portion of the first material from the first reception area (5) into the transporting/mixing area (9), wherein the further portion of the first material is mixed with the second part of the mixture,
controlling at least one of the test area (4) or the third reception area (7) so as to move the first part of the mixture into the third reception area (7),
controlling at least one of the transporting/mixing area (9) or the test area (4) in such a manner that the second part of the mixture is moved from the transporting/mixing area (9) into the test area (4) for detecting the response behavior of the electronic component sensor (3).

11. The method according to claim 9, wherein the steps according to claim 8 are repeated for creating a characteristic curve of the electronic component sensor (3).

12. The method according to claim 10, wherein the steps according to claim 8 are repeated for creating a characteristic curve of the electronic component sensor (3).

* * * * *